United States Patent
Penney et al.

(10) Patent No.: US 9,682,054 B2
(45) Date of Patent: Jun. 20, 2017

(54) MEDIUM-CHAIN LENGTH FATTY ACIDS, GLYCERIDES AND ANALOGUES AS STIMULATORS OF ERYTHROPOIESIS

(75) Inventors: Christopher Penney, Quebec (CA); Lyne Gagnon, Quebec (CA); Pierre Laurin, Quebec (CA); Boulos Zacharie, Quebec (CA)

(73) Assignee: PROMETIC PHARMA SMT LIMITED, Cambridge (GB)

( * ) Notice: Subject to any disclaimer, the term of this patent is extended or adjusted under 35 U.S.C. 154(b) by 1232 days.

(21) Appl. No.: 10/544,350

(22) PCT Filed: Feb. 6, 2004

(86) PCT No.: PCT/GB2004/000457
§ 371 (c)(1),
(2), (4) Date: Nov. 18, 2005

(87) PCT Pub. No.: WO2004/069237
PCT Pub. Date: Aug. 19, 2004

(65) Prior Publication Data
US 2006/0128800 A1  Jun. 15, 2006

Related U.S. Application Data

(60) Provisional application No. 60/445,454, filed on Feb. 7, 2003.

(51) Int. Cl.
*A61K 31/20* (2006.01)
*A61K 31/23* (2006.01)
*A61K 47/14* (2017.01)
*A61K 45/06* (2006.01)

(52) U.S. Cl.
CPC .............. *A61K 31/20* (2013.01); *A61K 31/23* (2013.01); *A61K 45/06* (2013.01); *A61K 47/14* (2013.01)

(58) Field of Classification Search
USPC ........................................................ 514/183
See application file for complete search history.

(56) References Cited

U.S. PATENT DOCUMENTS

| | | | |
|---|---|---|---|
| 4,871,768 A | 10/1989 | Bistrian et al. | |
| 5,011,852 A | 4/1991 | Park et al. | |
| 5,214,035 A | 5/1993 | Veatch | |
| 5,308,620 A * | 5/1994 | Yen ....................... | A61K 9/1611 424/484 |
| 5,318,781 A * | 6/1994 | Shah et al. .................... | 424/455 |
| 5,431,925 A | 7/1995 | Ohmori et al. | |
| 5,470,861 A | 11/1995 | Harmon | |
| 5,549,905 A | 8/1996 | Mark et al. | |
| 5,597,562 A | 1/1997 | Nomura et al. | |
| 5,631,219 A * | 5/1997 | Rosenthal et al. ........... | 424/85.2 |
| 5,756,474 A | 5/1998 | Furstenau | |
| 5,851,534 A | 12/1998 | Raheman et al. | |
| 6,060,459 A | 5/2000 | von Borstel et al. | |
| 6,113,891 A | 9/2000 | Burdick et al. | |
| 6,136,336 A | 10/2000 | Tanaka et al. | |
| 6,200,602 B1 | 3/2001 | Watts et al. | |
| 6,267,985 B1 | 7/2001 | Chen et al. | |
| 6,326,360 B1 | 12/2001 | Kanazawa et al. | |
| 6,479,540 B1 | 11/2002 | Constantinides et al. | |
| 6,725,510 B1 | 4/2004 | Clyburn | |
| 6,835,750 B1 | 12/2004 | Henderson | |
| 6,967,028 B2 | 11/2005 | Dulieu et al. | |
| 2002/0028236 A1 * | 3/2002 | Naeff et al. .................... | 424/450 |
| 2002/0039595 A1 * | 4/2002 | Keller ........................... | 424/450 |
| 2002/0039596 A1 * | 4/2002 | Hartounian et al. .......... | 424/450 |
| 2003/0211972 A1 * | 11/2003 | Backstrom et al. .............. | 514/2 |
| 2004/0052836 A1 | 3/2004 | Li et al. | |
| 2004/0147599 A1 | 7/2004 | Gagnon et al. | |

(Continued)

FOREIGN PATENT DOCUMENTS

| | | |
|---|---|---|
| JP | 8-208510 | 8/1996 |
| JP | 10-265380 | 10/1998 |
| WO | WO 89/02275 | 3/1989 |

(Continued)

OTHER PUBLICATIONS

Mizuno et al., Effects of salicylate and other enhancers on rectal absorption of erythropoietin in rats, 1992, Journal of Pharmacy and Pharmacology, vol. 44, No. 7, pp. 570-573.*
Nijhof et al., Isolation and Characterization of the Erythroid Progenitor cell: CFU-E, 1983, The Journal of Cell Biology, vol. 96, pp. 386-392.*
Bach et al., The Usefulness of dietary medium-chain triglycerides in body weight control: fact or fancy?, 1996, Journal of Lipid Research, vol. 37, pp. 708-726.*
Santos et al., 2003, International Journal of Pharmaceutics, vol. 260, Issue 1, pp. 1-4.*
Burcham et al., The Effect of Absorption Enhancers on the Oral Absorption of the GP IIB/IIA Receptor Antagonist, DMP 728, in Rats and Dogs, 1995, Pharmaceutical Research, vol. 12, No. 12, pp. 2065-2070.*

(Continued)

*Primary Examiner* — Jeffrey S Lundgren
*Assistant Examiner* — Meghan Finn
(74) *Attorney, Agent, or Firm* — Saliwanchik, Lloyd & Eisenschenk

(57) ABSTRACT

Use of a composition comprising a compound of any of formulae I, II, IIa, III and IIIa; or a combination thereof wherein each $R_1$ is independently $C_{7-11}$ alkyl; A and B are independently H or CO—$R_1$; $R_2$ is H or $C_{1-4}$ alkyl; M is a metal monocation (k=1) or dication (k=2); Y is 0 or NH; and Z is 0, NH, $CH_2O$ or a bond; for the manufacture of a medicament for stimulating erythropoiesis. Preferably, the composition further comprises human erythropoietin.

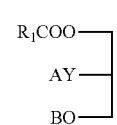

36 Claims, 5 Drawing Sheets

(56) References Cited

U.S. PATENT DOCUMENTS

| | | |
|---|---|---|
| 2008/0051324 A1 | 2/2008 | Penney et al. |
| 2008/0090848 A1 | 4/2008 | Penney et al. |

FOREIGN PATENT DOCUMENTS

| | | |
|---|---|---|
| WO | WO 95/30413 | 11/1995 |
| WO | WO 99/26640 | 6/1999 |
| WO | WO 99/45934 | 9/1999 |
| WO | WO 01/95914 | 12/2001 |
| WO | WO 02/083120 A2 | 10/2002 |
| WO | WO 02/083122 | 10/2002 |
| WO | WO 2005/012217 | 2/2005 |

OTHER PUBLICATIONS

Silvander et al., Vesicle Solubilization by Alkyl Sulfate Surfactants: A Cryo-TEM Study of the Vesicle to Micelle Transition, 1996, Journal of Colloid and Interface Science, vol. 179, pp. 104-113.*

Beau et al., "Comparison of Bone Marrow Toxicity of Medium-Chain and Long-Chain Triglyceride Emulsions: An In Vitro Study in Humans," *Journal of Parenteral and Enteral Nutrition*, 1997, vol. 21, No. 6, pp. 343-346.

Beers, "Leukopenia and Lymphocytopenia," *Merck Man. Diag. Ther.*, 1999, Chapter 135, pp. 931-933.

Demirer et al., "Comparison of the efficacy of medium chain triglycerides with long chain triglycerides in total parenteral nutrition in patients with hematologic malignancies undergoing peripheral blood stem cell transplantation," *Clinical Nutrition*, 2000, vol. 19, No. 4, pp. 253-258.

Hisha et al., "Isolation and Identification of Hematopoietic Stem Cell-Stimulating Substances from Kampo (Japanese Herbal) Medicine, Juzen-Taiho-To," *Blood*, 1997, vol. 90, pp. 1022-1030.

Keung et al., "Chemotherapy Treatment of Chyloperitoneum and Peritoneal Carcinomatosis Due to Cervical Cancer—Review of Literature," *Gynecologic Oncology*, 1996, vol. 61, pp. 448-450.

Kimoto et al., "Antitumor Effect of Medium-Chain Triglyceride and Its Influence on the Self-Defense System of the Body," *Cancer Detection and Prevention*, 1998, vol. 22, No. 3, pp. 219-224.

Pageau et al., "Systemic Protection against Radiation: II. Effect of Protein and Lipid Constituents of Diet," *Radiation Research*, May 1976, vol. 66, No. 2, pp. 267-273.

Reya et al., Abnormal Myelocytic Cell Development in Interleukin-2 (IL-2)-Deficient Mice: Evidence for the Involvement of IL-2 in Myelopoiesis, *Blood*, 1998, vol. 91, pp. 2935-2947.

Wanten et al., "Nutritional Lipid Emulsions Modulate Cellular Signaling and Activation of Human Neutrophils," *Journal of Lipid Research*, 2001, vol. 42, pp. 428-436.

Wanten etal., "Phagocytosis and Killing of *Candida albicans* by Human Neutrophils After Exposure to Structurally Different Lipid Emulsions," *Journal of Parenteral and Enteral Nutrition*, 2001, vol. 25, pp. 9-13.

Wanten et al., "Saturated triglycerides and fatty acids activate neutrophils depending on carbon chain-length," *European Journal of Clinical Investigation*, 2002, vol. 32, pp. 285-289.

Yamada et al., "Hematopoietic stem cell proliferation accelerator," Database Accession No. 124:97756 HCA, Nov. 16, 1995, corresponds to WO 95/30413.

Yanai et al., "Antitumor Effect of Arterial Administration of a Medium-Chain Triglyceride Solution of an Angiogenesis Inhibitor, TNP-470, in Rabbits Bearing VX-2 Carcinoma," *Pharmaceutical Research*, 1995, vol. 12, No. 5, pp. 653-657.

Duffy, K., et al., "Hydrazinonaphthalene and Azonaphthalene Thrombopoietin Mimics are Nonpeptidyl Promoters of Megakaryocytopoiesis," *J. Med. Chem.*, Sep. 13, 2001, pp. 3730-3745, vol. 44.

Duffy, K., et al., "Identification of a Pharmacophore for Thrombopoietic Activity of Small, Non-Peptidyl Molecules. 1. Discovery and Optimization of Salicylaldehyde Thiosemicarbazone Thrombopoietin Mimics," *J. Med. Chem.*, Jul. 19, 2002, pp. 3573-3575, vol. 45.

Henke M., et al., "Erythropoietin for patients undergoing radiotherapy: a pilot study" *Radiotherapy & Oncology*, 1999, pp. 185-190, vol. 50.

Ito, K., et al., "Maitake beta-glucan enhances granulopoiesis and mobilization of granulocytes by increasing G-CSF production and modulating CXCR4/SDF-1 expression," *Int Immunopharmacol.*, Jun. 30, 2009, pp. 1189-1196, vol. 9, No. 10.

Kusano, K., et al., "A potential therapeutic role for small nonpeptidyl compounds that mimic human granulocyte colony-stimulating factor," *Blood*, Sep. 25, 2003, pp. 836-842, vol. 103, No. 3.

Miller, K., et al., "Erythropoietin, with and without granulocyte-colony stimulating factor (G-CSF), in the treatment of myelodysplastic syndrome (MDS) patients" *Leukemia Research*, 1998, pp. S13-S16, vol. 22.

Office Action issued in U.S. Appl. No. 10/475,266, dated Nov. 2, 2009.

Pierelli, L., et al., "Erythropoietin Addition to Granulocyte Colony-Stimulating Factor Abrogates Life-Threatening Neutropenia and Increases Peripheral-Blood Progenitor-Cell Mobilization After Epirubicin, Paclitaxel, and Cisplatin Combination Chemotherapy: Results of a Randomized Comparison" *J. Clin. Oncology*, Apr. 1999, pp. 1288-1295, vol. 17, No. 4.

Wang, Y., et al., "Role of the spleen in cyclophosphamide-induced hematosuppression and extramedullary hematopoiesis in mice," *Arch Med Res.*, Jun. 4, 2009, pp. 249-255, vol. 40, No. 4.

* cited by examiner

MEDIUM-CHAIN LENGTH FATTY ACIDS, GLYCERIDES AND ANALOGUES AS STIMULATORS OF ERYTHROPOIESIS

This application is a National Stage Application of International Application Number PCT/GB2004/000457, filed Feb. 6, 2004; which claims the benefit of the filing date for U.S. Provisional Application Ser. No. 60/445,454, filed Feb. 7, 2003.

FIELD OF THE INVENTION

The present invention relates to the treatment of anemia. This includes the treatment of anemia associated with the use of chemotherapy and radiotherapy as well as the treatment of anemia arising from chronic renal failure or treatment of HIV-infected patients with AZT (zidovudine). The present invention also relates to reducing drug toxicity and enhancing drug efficiency. In particular, the present invention relates to the use of medium-chain length fatty acids such as capric acid, caprylic acid, or salts or triglycerides thereof or mono- or diglycerides or other analogues thereof as a stimulator of the production of erythrocyte progenitors, in particular Burst Forming Unit-Erythroid (Erythrocyte) cells or BFU-E cells.

BACKGROUND OF THE INVENTION

Chemotherapy refers to the use of cytotoxic agents such as, but not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin or chlorambucil in order to eradicate cancer cells and tumors. However, these agents are non-specific and, particularly at high doses, they are toxic to normal and rapidly dividing cells. This often leads to various side effects in patients undergoing chemotherapy and radiation therapy. Myelosuppression, a severe reduction of blood cell production in bone marrow, is one such side effect. It is characterized by anemia, leukopenia, neutropenia, agranulocytosis and thrombocytopenia. Severe chronic neutropenia is also characterized by a selective decrease in the number of circulating neutrophils and an enhanced susceptibility to bacterial infections.

The essence of treating cancer with chemotherapeutic drugs is to combine a mechanism of cytotoxicity with a mechanism of selectivity for highly proliferating tumor cells over host cells. However, it is rare for chemotherapeutic drugs to have such selectivity. The cytotoxicity of chemotherapeutic agents limits administrable doses, affects treatment cycles and seriously jeopardizes the quality of life for the cancer patient.

Although other normal tissues may also be adversely affected, bone marrow is particularly sensitive to proliferation-specific treatments such as chemotherapy or radiation therapy. Acute and chronic bone marrow toxicity is a common side effect of cancer therapies which leads to decreases in blood cell counts and anemia, leukopenia, neutropenia, agranulocytosis and thrombocytopenia One cause of such effects is a decrease in the number of replicating hematopoietic cells (e.g., pluripotent stem cells and other progenitor cells) caused by both a lethal effect of cytotoxic agents or radiation on these cells and by differentiation of stem cells provoked by a feed-back mechanism induced by the depletion of more mature marrow compartments. The second cause is a reduction in self-renewal capacity of stem cells, which is also related to both direct (mutation) and indirect (aging of stem cell population) effects (Tubiana, M., et al., *Radiotherapy and Oncology* 29:1-17, 1993). Thus, cancer treatments often result in a decrease in red blood cells or erythrocytes in the general circulation.

Erythrocytes are non-nucleated biconcave disk-like cells which contain hemoglobin and are essential for the transport of oxygen. Hemoglobin is a tetrapeptide which contains four binding sites for oxygen. Anemia refers to that condition which exists when there is a reduction below normal in the number of erythrocytes, the quantity of hemoglobin, or the volume of packed red blood cells in the blood as characterized by a determination of the hematocrit. The hematocrit or "red blood cell volume" is considered to be a particularly reliable indicator of anemia. Typically, in normal adults, average values for red blood cell count (millions/mm$^3$), hemoglobin (g/100 ml) and hematocrit or volume packed red blood cells (ml/100 ml) for females and males (at sea level) are 4.8±0.6 and 5.4±0.9, 14.0±2.0 and 16.0±2.0 and 42.0±5.0 and 47.0±5.0, as described in *Harrison's Principles of Internal Medicine*, 8$^{th}$ Edition, Appendix-Table A-5, McGraw Hill (1977). In normal humans, erythrocytes are produced by the bone marrow and released in the circulation, where they survive approximately 120 days. They are subsequently removed by the monocyte-phagocyte system.

Anemia is a symptom of various diseases and disorders. Therefore, anemia may be classified in terms of its etiology. For example, aplastic anemia is characterized by absence of regeneration of erythrocytes and is resistant to therapy. In such patients, there is a marked decrease in the population of myeloid, erythroid and thrombopoietic stem cells, which results in pancytopenia Hemolytic anemia arises from shortened survival of erythrocytes and the inability of the bone marrow to compensate for their decreased life span. It may be hereditary or may result from chemotherapy, infection or an autoimmune process. Iron deficiency anemia refers to a form of anemia characterized by low or absent iron stores, low serum iron concentration, low hemoglobin concentration or hematocrit, etc. Iron deficiency is the most common cause of anemia. Pernicious anemia, which most commonly affects adults, arises from a failure of the gastric mucosa to secrete adequate intrinsic factor, resulting in malabsorption of vitamin B12. Sickle cell anemia arises from a genetically determined defect in hemoglobin synthesis. It is characterized by the presence of sickle-shaped erythrocytes in the blood. The above are only exemplary of the many different anemias known to medicine. However, within the context of the current invention, it is of particular interest to address anemia associated with the use of chemotherapy or radiotherapy in the treatment of cancer. According to a statement published in *BioWorld Today* (page 4; Jul. 23, 2002), approximately 1.2 million cancer patients will undergo cytotoxic chemotherapy in the United States this year and about 800,000 or 67% of them will become anemic. Additionally, anemia is also associated with end-stage renal disease as is the case for patients who require regular dialysis or kidney transplantation for survival. This fills under the umbrella of chronic renal failure or the clinical situation in which there is a progressive and usually irreversible decline in kidney function.

Erythropoietin (EPO) is a glycoprotein with a molecular weight of 34,000 which is produced in the kidney. EPO stimulates the division and differentiation of committed erythroid progenitors in the bone marrow (BFU-E cells) and maintains cell viability (inhibition of apoptosis of BFU-E and CFU-E cells). The biological effects of EPO are receptor mediated. Amino acid identity amongst different animals is 92% between human EPO and monkey EPO and 80% between human EPO and mouse EPO. The primary stimulus for the biosynthesis of EPO is tissue hypoxia. However, as may be seen from the above, EPO has significant therapeutic potential for the treatment of certain anemias. For example, EPO can be used to treat anemia arising from a diminished endogenous production of EPO, which may result from a damaged or non-functional kidney (e.g., chronic renal failure as discussed above). Alternatively, EPO can be used to treat anemia arising from damaged bone marrow and subsequently diminished proliferation of erythrocyte progenitors (e.g., BFU-E cells) which results from treatment of cancer patients with cytotoxic chemotherapy or radiotherapy (as also discussed above). Various forms of recombinant EPO are available on the market. They differ by their expression system used for their manufacture and by their sites and degree of glycosylation of the protein. Epoetin alpha is expressed in CHO cells and is available under the trade name of Procrit®, Epogen® or Eprex®. Like EPO, Epoetin alpha has three N-linked glycosylation sites at asparagine (Asn) residues; Asn 19, Asn 33 and Asn 78. Epoietin beta is N-glycosylated at three sites but epoetin omega is N-glycosylated at Asn 24, Asn 28, Asn 83 and partially O-glycosylated at serine (Ser 126). Recently, a hyperglycosylated version of EPO has been approved which contains five N-linked glycosylation sites. It is a slow or extended release form of epoetin alpha available under the trade name of Aranesp®. This protein displays enhanced biological activity compared to the natural form, due to its approximately three-fold longer serum half-life. However, the use of these glycosylated proteins is expensive and restricted since they have to be produced by recombinant technology. Such post-therapeutic ameliorative treatments are unnecessary if patients are "chemoprotected" from immune suppression. Therefore, there is a need for novel compositions and methods to reduce the undesirable side effects of myelosuppressive states induced by chemotherapy and radiation therapy.

SUMMARY OF THE INVENTION

The present invention satisfies the need for chemoprotective agents by providing a novel method for the stimulation of the hematopoietic system in a mammal, including a human. The present invention also provides a novel method for treating the myelosuppressive effects of chemotherapy and radiotherapy and any other situation in which the stimulation of the hematopoietic system can be of therapeutic value such as, but not limited to, anemia.

In accordance with this method, a composition comprising capric acid, caprylic acid, or metallic salts (sodium, potassium, calcium, magnesium) or triglycerides thereof or mono- or diglycerides or alkyl esters or other analogues thereof in a pharmaceutically acceptable carrier is administered to a mammal, particularly humans, in an amount effective to significantly reduce the adverse effects of chemotherapy and radiation therapy.

Accordingly, it is an object of the present invention to provide compositions using capric acid, caprylic acid, or metallic salts (sodium, potassium, calcium, magnesium) or triglycerides thereof or mono- or diglycerides or alkyl esters or other analogues thereof for the production of chemoprotective pharmaceutical compositions as a single agent or as a combination of two or more agents with and/or without other chemotherapeutic agents or such drugs which induce a state of myelosuppression.

Another object of the present invention relates to the use of capric acid, caprylic acid or sodium salts or triglycerides thereof or mono- or diglycerides thereof or related compounds as a hematopoiesis stimulating factor.

Furthermore, the present invention includes compositions containing capric acid or caprylic acid or sodium salts or triglycerides thereof or mono- or diglycerides or other analogues thereof and the use of such compounds for the treatment of myelosuppression and subsequent anemia and immunosuppression.

It is an object of the present invention to provide a method effective for providing chemoprotection of a mammal, including a human.

Another object of the present invention is to provide a method effective for increasing the efficacy of chemotherapy and radiation therapy in a mammal, including a human.

Yet another object of the invention is to provide methods for using more usual doses or even increasing the dose of chemotherapeutic compositions necessary to achieve a better therapeutic benefit, while avoiding increased side effects.

Still another object of the present invention is to provide a method effective for reducing or eliminating chemotherapy-induced anemia in a mammal, including a human.

Another object of the present invention is to provide a method for treating anemia arising from chronic renal failure, especially in those patients with end-stage renal disease.

Yet another object of the present invention is to provide a method for treating anemia arising from other medical procedures such as orthopedic surgery or the use of other drugs such as AZT.

Finally, another object of the present invention is to provide a method that causes minimal or no adverse effects to the recipient.

These and other objects, features and advantages of the present invention will become apparent after a review of the following detailed description of the disclosed embodiment and the appended claims.

DETAILED DESCRIPTION OF THE INVENTION

Figure 1:
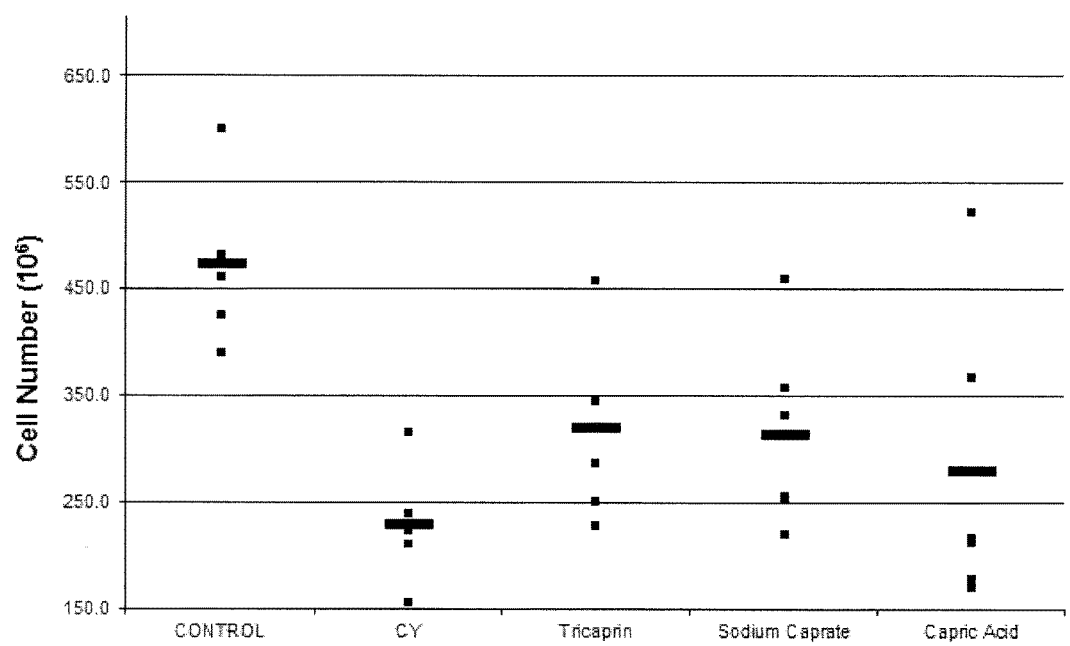
FIG. 1 illustrates a significant increase in spleen red cell count observed with oral pre-treatment with tricaprin, capric acid or sodium caprate in cyclophosphamide treated mice.

High dose chemotherapy and radiation destroy hematopoietic cells in bone marrow. Subsequently, the patient can be severely depleted in erythrocytes, platelets and neutrophils. Anemia results in fatigue, a lack of energy and shortness of breath. Thrombocytopenia leads to prolonged clotting time and bleeding disorders. Neutropenia places the patient at increased risk of infection. Myelosuppression is a dose-limiting factor in cancer treatment.

The present invention relates to a method of restoring the patient's hematopoietic system. Current methods employed to do the same make use of cytokines or glycoprotein growth factors. For example, erythropoietin can be used to stimulate the proliferation and maturation of responsive bone marrow erythroid cells. Erythropoietin is approved for human use for the treatment of anemia where appropriate: e.g., anemia arising from the inability to produce a sufficient number of erythrocytes. However, there are limitations which restrict the use of erythropoietin. Indeed, many of these limitations are common to the medical use of recombinant glycoprotein cytokines—availability, toxicity and efficacy, especially with chronic use. For example, some patients treated with recombinant human erythropoietin develop an immune response to the glycoprotein which results in pure red cell aplasia. When the latter occurs, the antibody developed to the recombinant protein also attacks the patient's equivalent or endogenous protein. Subsequently, the patient develops a worst anemia than before drug treatment.

Medium-chain triglyceride(s) (MCT) can be made by esterifying glycerol with fatty acids having carbon chain lengths of 8 (C8, octanoic acid or caprylic acid) or 10 (C10, decanoic acid or capric acid). MCT is usually a mixture of glycerol esters of C8 and C10 fatty acids; however, MCT can also contain small amounts (2±1% each) of glycerol esters of C6 (hexanoic acid or caproic acid) and C12 (dodecanoic acid or lauric acid). Long-chain triglyceride(s) (LCT), on the other hand, consist of glycerol esterified with fatty acids with carbon chain lengths of greater than 12 atoms. Typical fatty acids present in LCT include palmitic (C16) and stearic (C18) acids. Unlike MCT, LCT is the primary component of dietary fats. Indeed, MCT and LCT have significantly different biological properties. Some of the physiological differences between MCT and LCT are described in *Harrison's Principles of Internal Medicine*, $8^{th}$ Edition, 1520-1521 (1977); $15^{th}$ Edition, 1668-1669 (2001). For example, MCT, in contrast to LCT, do not require hydrolysis by pancreatic lipase, since they can be absorbed by intestinal epithelial cells.

MCT and their constituent medium-chain fatty acids are nontoxic materials which are used in the food and pharmaceutical industries. For example, Traul, K. A., et al. (*Food and Chemical Toxicology* 38:79-98, 2000) state that MCT have been utilized in an increasing number of food and nutrition applications because they offer a number of advantages over LCT. MCT are also used primarily as emulsifiers in various human and veterinary pharmaceutical preparations and in cosmetics. They refer to a number of toxicological studies which support the safety of MCT. For example, they note that the safety of human dietary consumption of MCT, up to levels of 1 g/kg, has been confirmed in clinical trials. C8 and C10 fatty acids possess similar safety and use. For example, in *The Merck Index*, $11^{th}$ Edition, 266 (1989) caprylic acid is reported to have an $LD_{50}$ (oral, rats)=10.08 g/kg which is essentially nontoxic. In fact, according to part 184 of the Code of Federal Regulations (CFR), the U.S. Food and Drug Administration (FDA) has granted caprylic acid a GRAS (Generally Recognized As Safe) affirmation. Similarly, according to part 172 (CFR) free fatty acids (e.g., capric, caprylic) and their metallic salts are recognized as safe additives for use in food. As noted by Dimitrijevic, D., et al. (*Journal of Pharmacy and Pharmacology* 53:149-154, 2001), capric acid (sodium salt) is approved for human use in Japan and Sweden as an absorption enhancer for rectal drug products. U.S. Pat. No. 4,602,040 (1986) describes the use of MCT as a pharmaceutical excipient. More recently, PCT publication WO 01/97799 describes the use of medium-chain fatty acids, in particular caprylic and capric acids, as antimicrobial agents.

However, until the unexpected findings disclosed herein, the effectiveness of medium-chain fatty acids such as capric acid, caprylic acid or metallic salts or mono-, di- or triglycerides (MCT) thereof or related compounds for the stimulation of production of erythrocytes from erythroid progenitor cells, or erythropoiesis, was unknown. As described herein, MCT may comprise triglycerides of C8 (caprylic) and C10 (capric) fatty acids which constitute at least 98% of the activity pertaining to the stimulation of hematopoiesis and erythropoiesis. The former activity was described in our PCT publication WO 02/83120, but stimulation of erythropoiesis and treatment of anemia was not previously described. Indeed, this discovery was completely unexpected since very little has been reported in the literature with regard to lower molecular weight or smaller molecules than glycoproteins being able to stimulate erythropoiesis. A synthetic dimeric form of an erythropoietin mimetic peptide (EMP) was described by Wrighton, N.C., et al. (*Nature Biotechnology* 15:1261-1265, 1997). Although considerably smaller than erythropoietin, EMP is a polypeptide which contains twenty amino acids in each monomer. More importantly, EMP is significantly less active than erythropoietin. More recently, PCT publication WO 02/19963 describes synthetic erythropoiesis protein (SEP) as a synthetic stabilized polypeptide with erythropoietin-like biological activity. The reported advantage of SEP is that it is a stabilized, relatively longer, half-life molecule which is made by chemical synthesis and not by relatively more expensive recombinant technology. Stabilization is achieved by the introduction of ethylene glycol units (e.g., PEG) and so this introduces an additional level of complexity into the preparation of SEP. In summary, the prior art teaches that the stimulation of production of erythrocytes requires the use of large polypeptide or protein molecules.

The present invention relates to the use of medium-chain fatty acids or metallic salts or triglycerides thereof or mono- or diglycerides or other analogues thereof or a MCT composition as a hematopoiesis activation or growth factor and, more particularly, as a stimulator of the production of erythrocyte progenitor cells. When used in chemotherapy and radiotherapy, medium-chain fatty acids or metallic salts or triglycerides thereof or mono- or diglycerides or other analogues thereof or MCT is administered before, during and/or after the treatment in order to shorten the period of anemia and to accelerate the replenishment of the hematopoietic system. Furthermore, it is possible to use a combination of medium-chain fatty acids along with their metallic salts or triglycerides thereof or mono- or diglycerides thereof or other analogues thereof and/or MCT at multiple points relative to treatment with chemotherapy and radiotherapy (e.g., fatty acids before treatment and MCT after). Alternatively, it is possible to administer the combination simultaneously: before, during and/or after treatment with chemotherapy and radiotherapy. In severe anemia arising from a diminished production of EPO, medium-chain fatty acids or metallic salts or triglycerides thereof or mono- or diglycerides or other analogues thereof or MCT is used as the therapeutic agent Medium-chain fatty acids or metallic salts or triglycerides thereof or mono- or diglycerides or other analogues thereof or MCT can also be used after bone marrow transplantation in order to stimulate bone marrow stem cells thus shortening the time period for recovery from anemia.

As used herein, "medium-chain fatty acids such as capric acid or caprylic acid or metallic salts or triglycerides thereof or mono- or diglycerides or other analogues thereof or MCT composition" refers to a composition comprising said active ingredient and one or more pharmaceutically acceptable carriers.

As used herein, the term "pharmaceutically acceptable carrier" refers to a substance that does not interfere with the physiological effects of medium-chain fatty acids such as capric acid or caprylic acid or metallic salts or triglycerides thereof or mono- or diglycerides or other analogues thereof or MCT composition and that is not toxic to mammals including humans.

The capric or caprylic acid or salts or triglycerides thereof or mono- or diglycerides or other analogues thereof or a MCT composition of the present invention may be formulated using capric or caprylic acid or salts or triglycerides thereof or mono- or diglycerides or other analogues thereof or MCT and pharmaceutically acceptable carriers by methods known to those skilled in the art (*Merck Index*, Merck & Co., Rahway, N.J.). These compositions include, but are not limited to, solids, liquids, oils, emulsions, gels, aerosols, inhalants, capsules, pills, patches and suppositories.

All methods include the step of bringing the active ingredient(s) into association with the carrier which constitutes one or more accessory ingredients.

As used herein, the term "chemotherapy" refers to a process of killing proliferating cells using a cytotoxic agent. The phrase "during the chemotherapy" refers to the period in which the effect of the administered cytotoxic agent lasts. On the other hand, the phrase "after the chemotherapy" is meant to cover all situations in which a composition is administered after the administration of a cytotoxic agent regardless of any prior administration of the same and also regardless of the persistence of the effect of the administered cytotoxic agent.

When the method of this invention is applied to chemotherapy, a capric or caprylic acid or salts or triglycerides thereof or mono- or diglycerides or other analogues thereof or a MCT composition can be administered prior to, during, or subsequent to the chemotherapy (i.e., prior to, during, or subsequent to the administration of a cytotoxic agent).

By "cytotoxic agent" is meant an agent which kills highly proliferating cells: e.g., tumors cells, virally infected cells, or hematopoietic cells. Examples of a cytotoxic agent which can be used to practice the invention include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin or chlorambucil, and an agonist of any of the above compounds. A cytotoxic agent can also be an antiviral agent e.g., AZT (i.e. 3'-azido-3'-deoxythymidine) or 3TC/lamivudine (i.e. 3-thiacytidine).

As used herein, the term "chemoprotection" refers to protection provided to a mammal from the toxic effects arising from treatment of the mammal with a chemotherapeutic agent Most often, the latter is a cytotoxic agent whose therapeutic effect arises from its ability to interfere with or inhibit some aspect of DNA replication, RNA transcription, or subsequent translation of protein. Therefore, a chemoprotective agent refers to any compound administered to a mammal which would protect the mammal, or facilitate the recovery of the animal, from the toxic effects resulting from treatment of the mammal with a chemotherapeutic agent.

Anemia can be diagnosed and its severity can be determined by a person skilled in the art. The term "anemia" may refer to that condition which exists when there is a reduction below normal in the number of erythrocytes, the quantity of hemoglobin, or the volume of packed red blood cells. Such clinical criteria are subject to variablity. Without limitation, anemia may be the result of a reduction in the mass of circulating red blood cell. Efficacy of treatment can also be determined by a person skilled in the art. It may provide a palliative effect.

In one preferred embodiment, the pharmaceutical composition is in the form of any suitable composition for oral, sublingual, rectal, topical administration or inhalation (nasal spray), intramuscular, intradermal, subcutaneous or intravenous administration for use in the treatment of anemia.

It will be appreciated that the amount of a composition of the invention required for use in the treatment will vary with the route of administration, the nature of the condition being treated, the age and condition of the patient, and will ultimately be at the discretion of the attending physician. The desired dose may be conveniently presented in a single dose or as divided doses taken at appropriate intervals, for example as two, three or more doses per day as necessary to effect or bring about treatment. The term "treatment" or "treating" includes any therapy of existing disease or condition and prophylaxis of the disease or condition (e.g., anemia) in a mammal. This includes (a) preventing the disease or condition from occurring in a patient which may be predisposed to the disease but has not yet been diagnosed as having it, (b) inhibiting or arresting the development of the disease or condition and (c) relieving the disease or condition by causing its regression or the amelioration of one or more symptoms.

While it is possible that, for use in therapy, medium-chain fatty acids or metallic salts or triglycerides thereof or mono- or diglycerides or other analogues thereof or MCT may be administered as the raw chemical, it is preferable to present the active pharmaceutical ingredient as a pharmaceutical formulation or composition. A nontoxic composition is formed by the incorporation of any of the normally employed excipients such as, for example but not limited to, mannitol, lactose, trehalose, starch, magnesium stearate, talcum, cellulose, carboxymethyl cellulose, glucose, gelatin, sucrose, glycerol magnesium carbonate, sodium citrate, sodium acetate, sodium chloride, sodium phosphate and glycine.

In a preferred embodiment of the invention, the amount of active ingredient administered is such that the concentration in the blood (free and/or bound to serum albumin) is greater than 1 $\mu$M In other embodiments, the concentration in the blood may be greater than 1 mM In another preferred embodiment of the invention, it might be necessary to achieve a sufficient local concentration of an active pharmaceutical ingredient to obtain a biologically or medically significant effect in a target tissue (e.g. bone marrow). Such a relatively high concentration of active pharmaceutical ingredient may be required, at least at the target tissue, as it may be necessary for the capric acid or caprylic acid or salts or triglycerides thereof or mono- or diglycerides or other analogues thereof or a MCT composition of the present invention to form a micelle or aggregate structure in order to elicit a biological response. A single dose may be comprised of a total amount from about 1 g to about 10 g of active ingredient (and any intermediate ranges thereof).

In another embodiment, the pharmaceutical composition is in a form suitable for enteral, mucosal (including sublingual, pulmonary and rectal) or parenteral (including intramuscular, intradermal, subcutaneous and intravenous) administration. The formulations may, where appropriate, be conveniently presented in discrete dosage units and may be prepared by any of the methods well known in the art of pharmacy. All methods include the step of bringing into association the active pharmaceutical ingredient with liquid carriers or finely divided solid carriers or both and then, if necessary, shaping the product into the desired form. When desired, the above-described formulations adapted to give sustained release of the active pharmaceutical ingredient may be employed. Sustained release formulations well known to the art include the use of liposomes, biocompatible polymers, a bolus injection or a continuous infusion.

Medium-chain fatty acids or salts or triglycerides thereof or mono- or diglycerides or other analogues or MCT can also be used in combination with other therapeutically active agents such as cytotoxic anticancer agents or other anticancer agents (immune modulating or regulating drugs or therapeutic vaccines or anti-angiogenesis drugs, etc.) or immune suppressive drugs (including anti-inflammatory drugs). The individual components of such combinations may be administered either sequentially or simultaneously in separate or combined pharmaceutical formulations. The combination referred to above may conveniently be presented for use in the form of a pharmaceutical formulation and thus pharmaceutical formulations comprising a combination defined above together with a pharmaceutically acceptable carrier thereof comprise a further aspect of the invention.

EXAMPLES

The following further illustrate the practice of this invention but are not intended to be limiting thereof.

Example 1: Chemoprotection Studies: In Vivo Induction of Immune Cell Proliferation or Protection by MCT Female C57BL/6 mice, 6 to 8 week old, were immunosuppressed by treatment with 200 mg/kg of cyclophosphamide (CY) or 80 mg/kg 5-fluorouracil (5-FU) administered intravenously at day 0. To examine the immunoprotective effect of MCT or other compounds, mice were pre-treated orally at day −3, −2 and −1 at day 0 with the compound. Mice were sacrificed at day +5 by cardiac puncture and cervical dislocation. Then, a gross pathological observation of the femurs (as a source of bone marrow cells) was recorded.

Table 1 represents the gross pathological observation of the femurs obtained in cyclophosphamide immunosuppressed animals in the presence or in the absence of compounds. Results show that the femur of a normal mouse has a vivid red color, demonstrating the proliferative state of the hematopoietic progenitor cells and their progeny. When treated with cyclophosphamide, the bone marrow is depleted from hematopoietic cells and has a transparent "white" appearance indicating a suppression of the proliferation of hematopoietic progenitors originating from the bone marrow. However, under cytotoxic-induced immunosuppressive conditions, the addition of MCT, tricaprylin, tricaprin, capric acid or sodium caprate reversed the effect of cyclophosphamide. This resulted in a red appearance of the femur, indicating the expansion of hematopoietic progenitor cells, in particular the erythrocyte population. The same results are observed when immunosuppression is induced by 5-fluorouracil (5-FU).

TABLE 1

Effect of cyclophosphamide (CY), CY + MCT, CY + tricaprylin, CY + tricaprin, CY + capric acid and CY + sodium caprate on the appearance of bone marrow from the femur: gross pathological observation.

Gross pathological observations: Bone Marrow Color

| Control | Vivid red |
| --- | --- |
| CY | White, almost translucent |
| CY + MCT | Red |
| CY + tricaprylin | Red |
| CY + tricaprin | Red |
| CY + capric acid | Red |
| CY + sodium caprate | Red |

Example 2: Chemoprotection Studies: In Vivo Induction of Immune Cell Proliferation or Protection: Comparison of Tricaprin, Capric Acid and Sodium Caprate Effect of tricaprin, capric acid and sodium caprate on in vivo induction of immune cell proliferation or protection was undertaken following the protocol described in example 1. After the sacrifice, tissues were crushed in PBS buffer and cells were counted on a hemacytometer.

A significant increase in spleen red cell count was observed with oral pre-treatment with tricaprin, capric acid or sodium caprate in cyclophosphamide treated mice (FIG. 1). Further, some treated animals return to a "baseline level" in terms of the spleen red cell count as compared to non-immunosuppressed animals (control).

Figure 2:
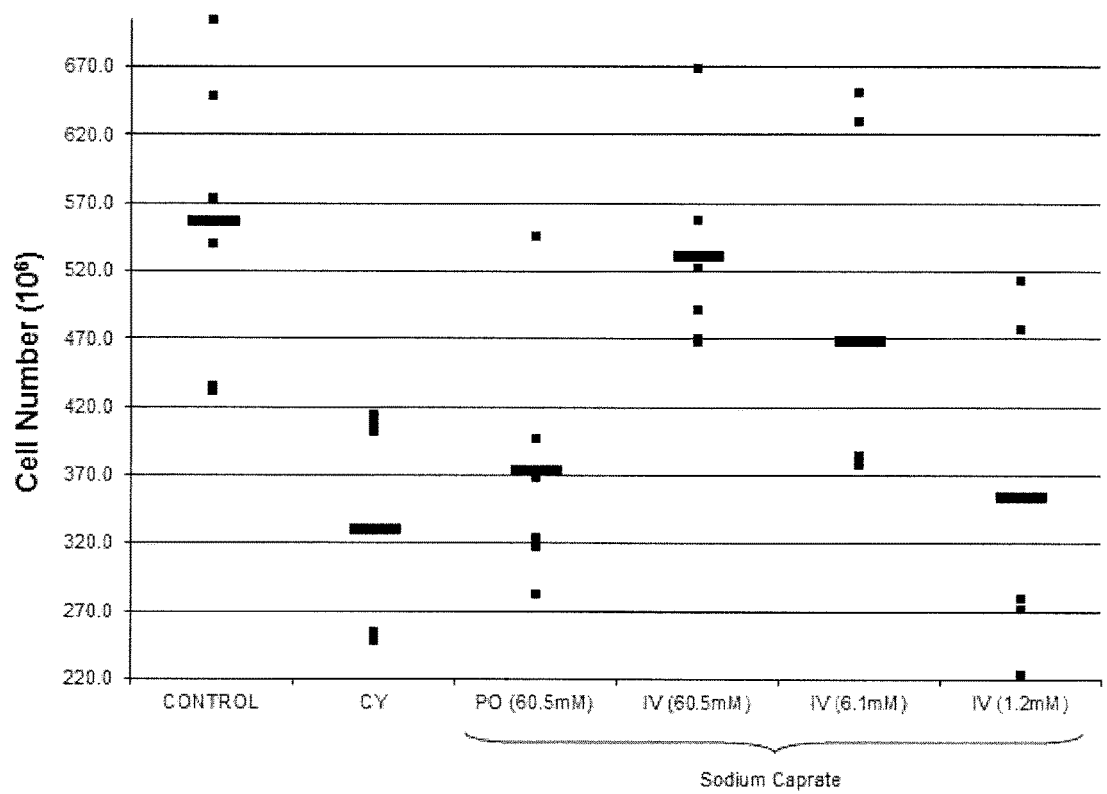
FIG. 2 illustrates a significant increase in proliferation of spleen red cell count observed with oral and intravenous administration pre-treatments with sodium caprate in cyclophosphamide treated mice.

Example 3: Chemoprotection Studies: In Vivo Induction of Immune Cell Proliferation or Protection: Oral and Intravenous Dose-Response of Sodium Caprate Effect of oral and intravenous administration of sodium caprate on in vivo induction of immune cell proliferation or protection was undertaken following the protocol described in example 1. After sacrifice, tissues were crushed in PBS buffer and cells were counted on a hemacytometer. A significant increase in proliferation of spleen red cell count was observed with oral and intravenous administration pre-treatments with sodium caprate in cyclophosphamide treated mice (FIG. 2). Furthermore, intravenous administration of sodium caprate increases the spleen red cell counts to the baseline level of control mice (non-immunosuppressed).

Figure 3:
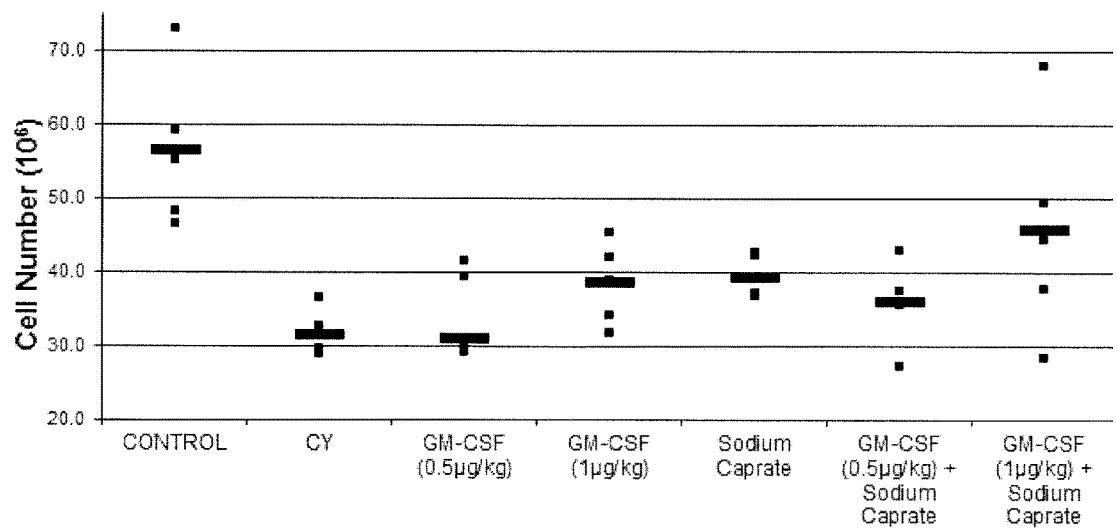
FIG. 3 illustrates a significant increase in bone marrow red cell count was observed with sodium caprate and GM-CSF (high concentration, 1 μg/kg) in cyclophosphamide treated mice.

Example 4: Chemoprotection Studies: In Vivo Induction of Erythrocyte Proliferation or Repopulation: Comparison with GM-CSF Effect of oral and intravenous administration of sodium caprate and GM-CSF on in vivo induction of immune cell proliferation or protection was undertaken following the protocol described in example 1. After sacrifice, tissues were crushed in PBS buffer and cells were counted on a hemacytometer. A significant increase in bone marrow red cell count was observed with sodium caprate and GM-CSF (high concentration, 1 µg/kg) in cyclophosphamide treated mice (FIG. 3). Furthermore, when used in combination with GM-CSF, an additive increase in bone marrow red cell count occurs.

Figure 4:
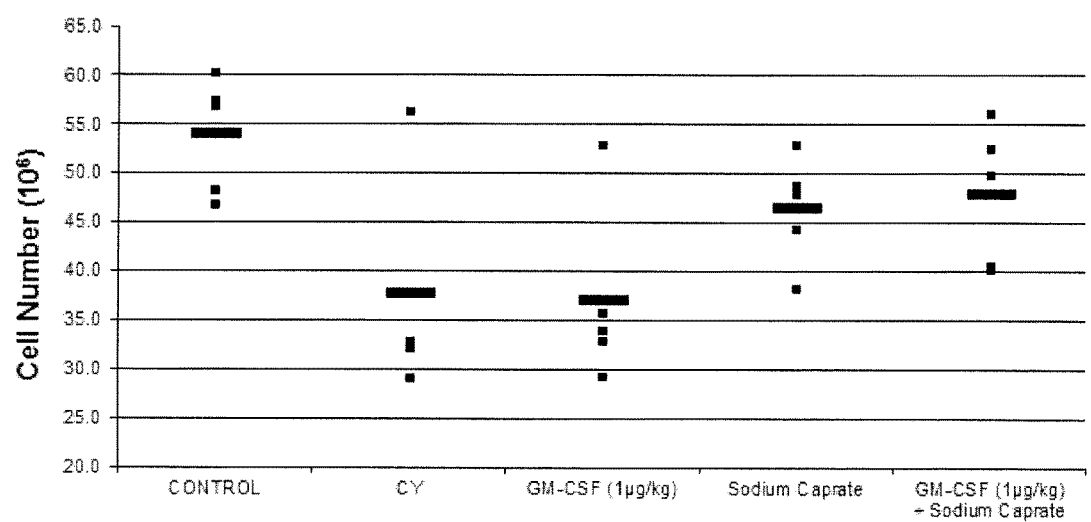
FIG. 4 illustrates a significant increase in the number of peripheral blood cell when sodium caprate was used alone.

Additionally, sodium caprate, when used alone, was able to induce a significant increase in the number of peripheral blood cell as demonstrated in FIG. 4.

Example 5: Anemia Model: Ex Vivo Induction of Bone Marrow Colony Forming Unit (CFU) Proliferation/Differentiation or Protection by Sodium Caprate To examine the immunoprotective or immunorestorative effect of sodium caprate in an anemia model, BALB/c mice were pre-treated intravenously at day −3, −2 and −1 with compound. Anemia was induced by treatment with 60 mg/kg phenylhydrazine administered intraperitoneally at day 0 to female BALB/c mice, 6 to 8 week old. Mice were sacrificed at day +6 by cardiac puncture and cervical dislocation. Then, bone marrow cells were obtained from femur. Cells were flushed and washed with PBS. Based on the viable cells count, the cells were resuspended at a concentration of $5 \times 10^5$ cells per ml in IMDM media supplemented with 2% FBS. From these cells, two replicates of $3 \times 10^4$ cells per dish were plated in Methocult medium so that a colony forming unit (CFU) formation assay could be undertaken. CFU-E and BFU-E were recorded after 2 to 3 days culture. CFU-GM and CFU-GEMM were recorded after 14 to 16 days culture.

Figure 5:
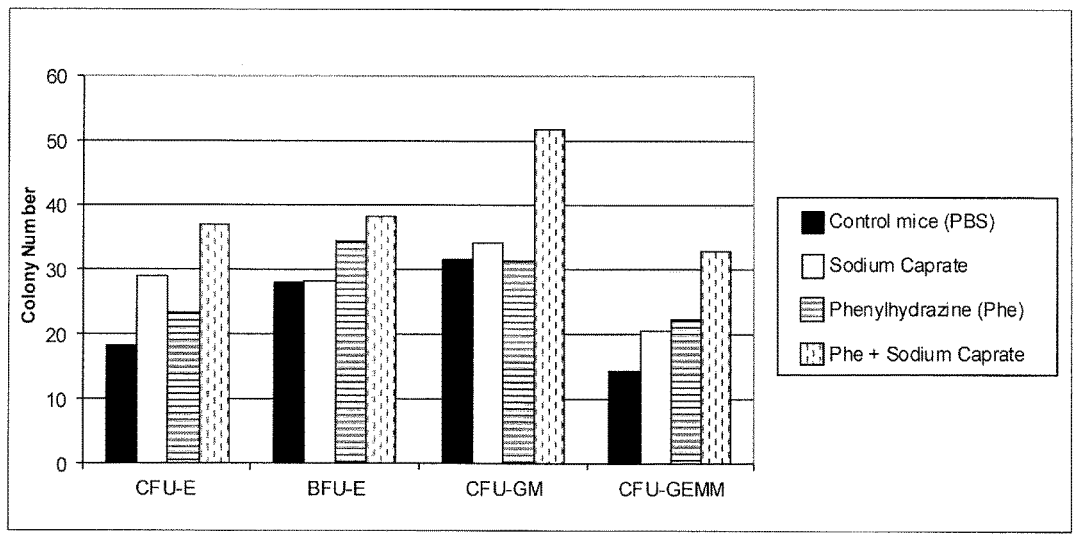
FIG. 5 illustrates an enhanced number of CFU-E and CFU-GEMM in normal mice when sodium caprate is used.

As illustrated in FIG. 5, sodium caprate enhances the number of CFU-E and CFU-GEMM in normal mice. In phenylhydrazine-induced anemia mice, sodium caprate induces a strong increase in CFU-E, CFU-GM and CFU-GEMM.

Example 6: Tricaprin and Tricaprylin Increase the Proliferation of In Vitro Human Bone Marrow Cells Bone marrow cells were obtained from the sternum of cancer patients. Cells were washed with PBS and resuspended at a concentration of $2 \times 10^6$ cells per ml. Cells were cultured in RPMI/FBS media in the presence or the absence of tricaprin or tricaprylin for 48 and 72 hours at 37° C. After incubation, cells were pulsed with 1 µCi of [$^3$H]-thymidine for 6 hours. Plates were harvested on a Tomteck and counted on a Microbeta β-counter. Incorporation of [$^3$H]-thymidine in the DNA is a direct indication of the cell proliferation.

Figure 6:
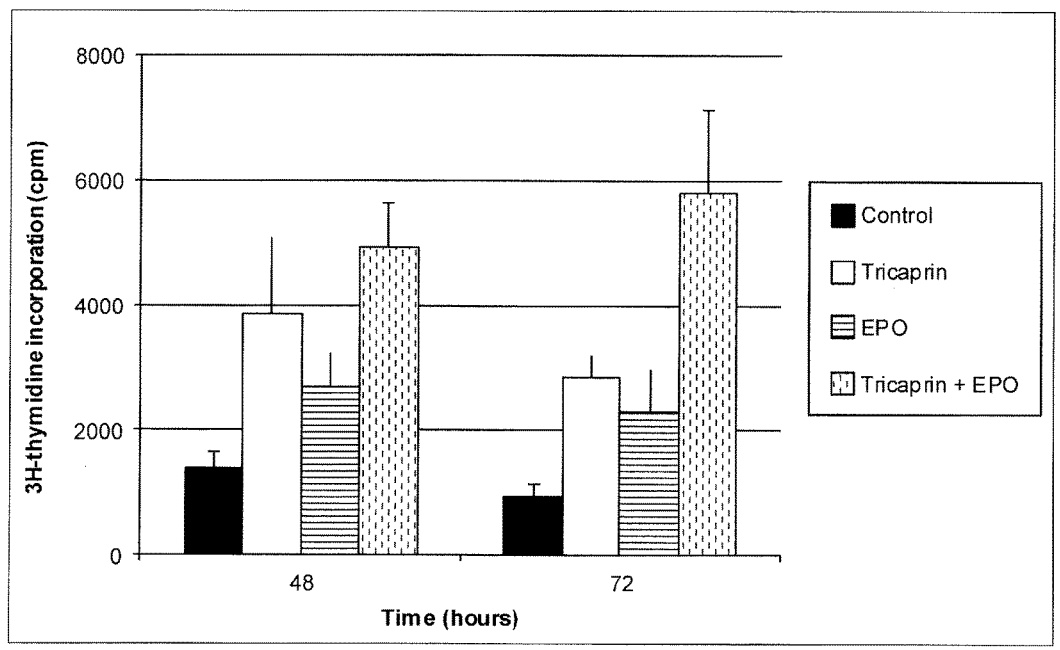
FIG. 6 represents a typical experiment on the effect of tricaprin on bone marrow proliferation.

FIG. 6 represents a typical experiment on the effect of tricaprin on bone marrow proliferation. Tricaprin increases bone marrow proliferation by 3 to 4 fold relative to the control. Furthermore, when used in combination with erythropoietin (EPO), an additive or synergistic increase in bone marrow proliferation occurs at 48 and 72 hours respectively.

Figure 7:
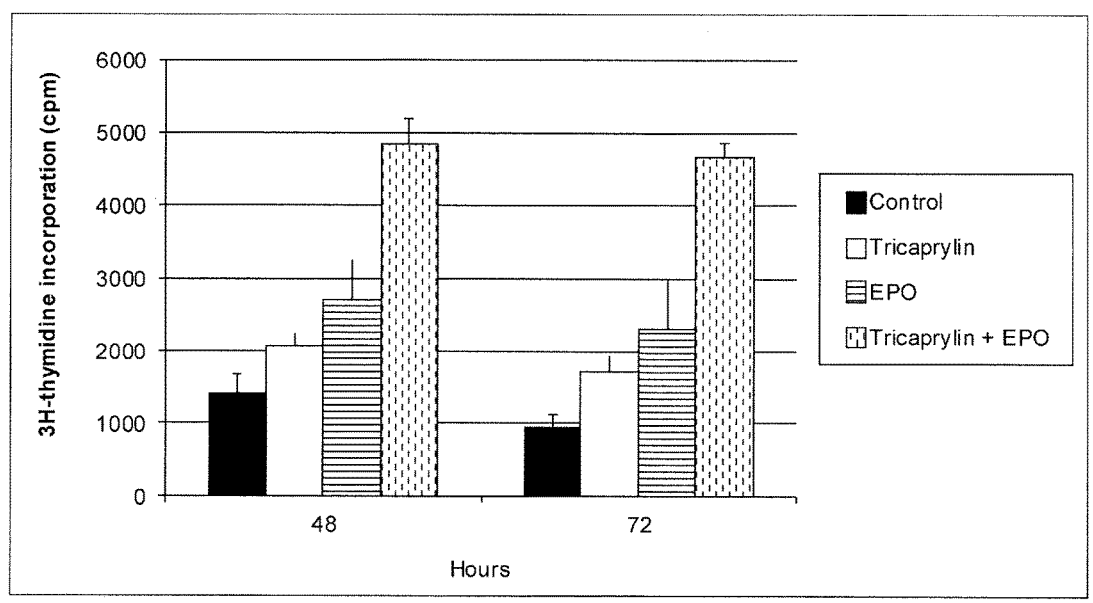
FIG. 7 represents a typical experiment on the effect of tricaprylin on bone marrow proliferation.

FIG. 7 represents a typical experiment on the effect of tricaprylin on bone marrow proliferation. Tricaprylin increases bone marrow proliferation by 2 fold relative to the control. Furthermore, when used in combination with erythropoietin (EPO), a synergistic increase in bone marrow proliferation occurs.

Example 7: Tricaprin Increases the Proliferation of In Vitro Human Bone Marrow BFU-E (Red Blood Cell Progenitor) Colony Formation and CFU-GEMM Bone marrow cells were obtained from the sternum of various cancer patients. Cells were washed with PBS and resuspended at a concentration of $2 \times 10^6$ cells per ml. Cells were cultured in RPMI/FBS or Myelocult (Stem cell technology, Vancouver)/FBS media in the presence or the absence of tricaprin for 5 days at 37° C. After incubation, cells were harvested, washed and counted. Based on the viable cells count, the cells were resuspended at a concentration of $5 \times 10^5$ cells per ml in IMDM media supplemented with 2% FBS. From these cells, four replicates of $2.5 \times 10^4$ cells per dish were plated in Methocult medium so that a colony forming unit (CFU) formation assay could be undertaken. CFU-GM, CFU-GEMM and BFU-E were recorded after 14 to 16 days culture.

Tables 2 and 3 represent two experiments on the effect of tricaprin on bone marrow cell colony formation in RPMI/FBS medium. The presence of tricaprin increases the number of CFU-GEMM (up to 3 times) and BFU-E colonies formation (up to 13 times). The latter cells are the progenitors of the red blood cells.

Tables 4 and 5 represent two experiments which demonstrate the effect of tricaprin on bone marrow cell colony formation in Myelocult/FBS medium, which is a more enriched medium (supplemented with additional growth factors). The presence of tricaprin increases the number of CFU-GEMM (up to 2 times) and BFU-E colonies formation (up to 6 times), which are the progenitors of the red blood cells.

TABLE 2

Effect of tricaprin on in vitro human hematopoietic progenitors (CFU formation) cultured in RPMI/FBS medium.

| EXPERIMENT 1 | BFU-E | CFU-GM | CFU-GEMM | TOTAL CFC* |
|---|---|---|---|---|
| Control | 10 | 26 | 1.25 | 38 |
| Tricaprin 10% | 130 | 26 | 4.75 | 161 |

TABLE 3

Effect of tricaprin on in vitro human hematopoietic progenitors (CFU formation) cultured in RPMI/FBS medium.

| EXPERIMENT 2 | BFU-E | CFU-GM | CFU-GEMM | TOTAL CFC* |
|---|---|---|---|---|
| Control | 15 | 32 | 1.25 | 49 |
| Tricaprin 10% | 121 | 25 | 4 | 150 |

TABLE 4

Effect of tricaprin on in vitro human hematopoietic progenitors (CFU formation) cultured in Myelocult/FBS medium.

| EXPERIMENT 1 | BFU-E | CFU-GM | CFU-GEMM | TOTAL CFC* |
|---|---|---|---|---|
| Control | 54 | 41 | 2.5 | 98 |
| Tricaprin 10% | 380 | 17 | 4.75 | 401 |

TABLE 5

Effect of tricaprin on in vitro human hematopoietic progenitors (CFU formation) cultured in Myelocult/FBS medium.

| EXPERIMENT 2 | BFU-E | CFU-GM | CFU-GEMM | TOTAL CFC* |
|---|---|---|---|---|
| Control | 49 | 26 | 2.5 | 77 |
| Tricaprin 10% | 268 | 34 | 4.25 | 306 |

*CFC = Colony Forming Cells

The invention claimed is:

1. A method for stimulating erythropoiesis wherein said method comprises administering, to a subject who is anemic, a composition comprising a compound of any of formulae I, II, and IIa, or a combination thereof;

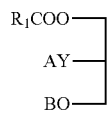   I

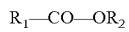   II

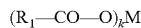   IIa wherein each $R_1$ is independently $C_{7-11}$ alkyl;
A and B are independently H or CO—$R_1$;
$R_2$ is H or $C_{1-4}$ alkyl;
M is a metal monocation (k=1) or (k=2); and
Y is O;
wherein the administration of said composition is done by a route selected from sublingual, pulmonary, intramuscular, intradermal, subcutaneous and intravenous; wherein each dose of said composition that is administered comprises about 1 gram to about 10 grams of said compound(s); and wherein the administration of said compound(s) causes stimulation of erythropoiesis.

2. The method according to claim 1, wherein the composition comprises a compound of formula II, wherein $R_2$ is hydrogen and which is a medium-chain fatty acid.

3. The method according to claim 1, wherein the composition comprises a compound of formula IIa, and wherein M is a metallic counterion selected from the group consisting of calcium, magnesium, potassium, and sodium.

4. The method according to claim 1, wherein the composition comprises caprylic acid or capric acid.

5. The method according to claim 1, wherein the composition comprises sodium caprylate or sodium caprate.

6. The method according to claim 1, wherein the composition comprises calcium caprylate or calcium caprate.

7. A method for stimulating erythropoiesis wherein said method comprises administering, to a subject who is anemic, a composition comprising a compound of any of formulae I, II, and IIa, or a combination thereof;

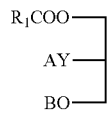   I

   II

   IIa wherein each $R_1$ is independently $C_{7-11}$ alkyl;
A and B are independently H or CO—$R_1$;
$R_2$ is H or $C_{1-4}$ alkyl;
M is a metal monocation (k=1) or (k=2); and
Y is O;
wherein the administration of said composition is done orally, and said oral administration is not accompanied with erythropoietin; wherein each dose of said composition that is administered comprises about 1 gram to about 10 grams of said compound(s); and wherein the administration of said compound(s) causes stimulation of erythropoiesis.

8. The method according to claim 7, wherein the subject is receiving chemotherapy.

9. The method according to claim 7, wherein the subject is receiving radiotherapy.

10. The method according to claim 7, wherein the subject has chronic anemia.

11. The method according to claim 7, wherein the subject has transient anemia.

12. The method according to claim 7, wherein the subject has chronic renal failure.

13. The method according to claim 7, wherein the subject has anemia arising from end-stage renal disease.

14. The method according to claim 1, wherein the subject is receiving chemotherapy.

15. The method according to claim 1, wherein the subject is receiving radiotherapy.

16. The method according to claim 1, wherein the subject has chronic anemia.

17. The method according to claim 1, wherein the subject is a human.

18. The method according to claim 7, wherein the subject is a human.

19. A method for stimulating erythropoiesis wherein said method comprises administering, to a subject who is anemic, a composition comprising a compound of any of formulae I, II, and IIa, or a combination thereof;

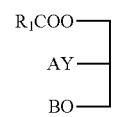   I

   II

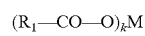   IIa wherein each $R_1$ is independently $C_{7-11}$ alkyl;
A and B are independently H or CO—$R_1$;
$R_2$ is H or $C_{1-4}$ alkyl;
M is a metal monocation (k=1) or (k=2); and
Y is O,
wherein the administration of said composition is done orally, and said oral administration is not accompanied with erythropoietin; wherein the anemic condition of the subject does not result from iron-deficiency; and wherein the administration of said compound(s) causes stimulation of erythropoiesis.

20. The method according to claim 19, wherein the subject is receiving chemotherapy.

21. The method according to claim 19, wherein the subject is receiving radiotherapy.

22. The method according to claim 19, wherein the subject has chronic anemia.

23. The method according to claim 19, wherein the subject has transient anemia.

24. The method according to claim 19, wherein the subject has chronic renal failure.

25. The method according to claim 19, wherein the subject has anemia arising from end-stage renal disease.

26. The method according to claim 19, wherein the subject is a human.

27. The method according to claim 7, wherein the composition comprises a compound of formula II, wherein $R_2$ is hydrogen and which is a medium-chain fatty acid.

28. The method according to claim 7, wherein the composition comprises a compound of formula IIa, and wherein M is a metallic counterion selected from the group consisting of calcium, magnesium, potassium, and sodium.

29. The method according to claim 7, wherein the composition comprises caprylic acid or capric acid.

30. The method according to claim 7, wherein the composition comprises sodium caprylate or sodium caprate.

31. The method according to claim 7, wherein the composition comprises calcium caprylate or calcium caprate.

32. The method according to claim 19, wherein the composition comprises a compound of formula II, wherein $R_2$ is hydrogen and which is a medium-chain fatty acid.

33. The method according to claim 19, wherein the composition comprises a compound of formula IIa, and wherein M is a metallic counterion selected from the group consisting of calcium, magnesium, potassium, and sodium.

34. The method according to claim 19, wherein the composition comprises caprylic acid or capric acid.

35. The method according to claim 19, wherein the composition comprises sodium caprylate or sodium caprate.

36. The method according to claim 19, wherein the composition comprises calcium caprylate or calcium caprate.

* * * * *

UNITED STATES PATENT AND TRADEMARK OFFICE
CERTIFICATE OF CORRECTION

| | | |
|---|---|---|
| PATENT NO. | : 9,682,054 B2 | Page 1 of 1 |
| APPLICATION NO. | : 10/544350 | |
| DATED | : June 20, 2017 | |
| INVENTOR(S) | : Christopher Penney et al. | |

It is certified that error appears in the above-identified patent and that said Letters Patent is hereby corrected as shown below:

Column 1,
Line 59, "thrombocytopenia One" should read -- thrombocytopenia. One --.

Column 2,
Line 32, "pancytopenia Hemolytic" should read -- pancytopenia. Hemolytic --.
Line 57, "This fills" should read -- This falls --.

Column 8,
Line 50, "1 µM In other" should read -- 1 µM. In other --.
Line 51, "1 µM In another" should read -- 1 µM. In another --.

Signed and Sealed this
Sixth Day of March, 2018

Andrei Iancu
*Director of the United States Patent and Trademark Office*